United States Patent
Pathak et al.

(10) Patent No.: US 10,532,465 B2
(45) Date of Patent: *Jan. 14, 2020

(54) HANDHELD TOOL FOR LEVELING UNCOORDINATED MOTION

(71) Applicant: Verily Life Sciences LLC, Mountain View, CA (US)

(72) Inventors: Anupam J. Pathak, Mountain View, CA (US); Michael M. Allen, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 125 days.

This patent is subject to a terminal disclaimer.

(21) Appl. No.: 15/434,764

(22) Filed: Feb. 16, 2017

(65) Prior Publication Data

US 2017/0157774 A1 Jun. 8, 2017

Related U.S. Application Data

(62) Division of application No. 14/668,516, filed on Mar. 25, 2015, now Pat. No. 9,943,430.

(51) Int. Cl.
*B25J 11/00* (2006.01)
*A61H 3/00* (2006.01)
(Continued)

(52) U.S. Cl.
CPC .......... *B25J 11/0045* (2013.01); *A47G 21/02* (2013.01); *A61F 4/00* (2013.01); *A61H 3/00* (2013.01);
(Continued)

(58) Field of Classification Search
CPC ..... A47G 21/02; A47G 2200/046; A61F 4/00; A61H 2201/1253; A61H 2201/1481;
(Continued)

(56) References Cited

U.S. PATENT DOCUMENTS

| 3,711,638 A | 1/1973 | Davies |
| 4,479,797 A | 10/1984 | Kobayashi et al. |

(Continued)

FOREIGN PATENT DOCUMENTS

| AT | 411 011 B | 9/2003 |
| CN | 203646979 U | 6/2014 |

(Continued)

OTHER PUBLICATIONS

EP 16202985.4—Extended European Search Report, dated Mar. 23, 2017, 7 pages.

(Continued)

*Primary Examiner* — Brian W Wathen
*Assistant Examiner* — Chad G Erdman
(74) *Attorney, Agent, or Firm* — Christensen O'Connor Johnson Kindness PLLC (57) ABSTRACT

A handheld tool includes a handle for holding by a user, an attachment arm extending from the handle that is configured to connect to a user-assistive device, a first inertial measurement unit ("IMU") mounted to the attachment arm to acquire measurements of one or more of a motion or an orientation of the user-assistive device and to generate feedback data indicative of the measurements, an actuator assembly coupled to manipulate the user-assistive device via the attachment arm in at least two orthogonal dimensions, and a motion control system coupled to receive the feedback data from the first IMU and coupled to provide commands to the actuator assembly to provide auto-leveling of the user-assistive device to a frame of reference while the user manipulates the handheld tool.

22 Claims, 5 Drawing Sheets

(51) Int. Cl.
*A61J 7/00* (2006.01)
*B25J 1/04* (2006.01)
*B25J 13/08* (2006.01)
*G09B 19/00* (2006.01)
*A61F 4/00* (2006.01)
*A47G 21/02* (2006.01)
*A61B 5/11* (2006.01)

(52) U.S. Cl.
CPC . *A61J 7/00* (2013.01); *B25J 1/04* (2013.01); *B25J 13/088* (2013.01); *G09B 19/003* (2013.01); *A47G 2200/046* (2013.01); *A61B 5/1101* (2013.01); *A61H 2201/1253* (2013.01); *A61H 2201/1481* (2013.01); *A61H 2201/5064* (2013.01); *A61J 2200/70* (2013.01)

(58) Field of Classification Search
CPC ............... A61H 2201/5064; A61H 3/00; A61J 2200/70; A61J 7/00; B25J 11/0045; B25J 13/088; B25J 1/04; G09B 19/003
See application file for complete search history.

(56) References Cited

U.S. PATENT DOCUMENTS

| | | |
|---|---|---|
| 4,766,708 A | 8/1988 | Sing |
| 5,148,715 A | 9/1992 | Blaser et al. |
| 5,282,711 A | 2/1994 | Frische |
| 5,316,479 A | 5/1994 | Wong et al. |
| 5,562,707 A | 10/1996 | Prochazka et al. |
| 5,630,276 A | 5/1997 | Weinstein |
| 5,691,898 A | 11/1997 | Rosenberg et al. |
| 5,934,250 A | 8/1999 | Fujikawa et al. |
| 6,234,045 B1 | 5/2001 | Kaiser |
| 6,238,384 B1 | 5/2001 | Peer |
| 6,458,089 B1 | 10/2002 | Ziv-Av |
| 6,547,782 B1 | 4/2003 | Taylor |
| 6,695,794 B2 | 2/2004 | Kaiser et al. |
| 6,697,048 B2 | 2/2004 | Rosenberg et al. |
| 6,697,748 B1 | 2/2004 | Rosenberg et al. |
| 6,704,001 B1 | 3/2004 | Schena et al. |
| 6,704,002 B1 | 3/2004 | Martin et al. |
| 6,730,049 B2 | 5/2004 | Kalvert |
| 6,740,123 B2 | 5/2004 | Davalli et al. |
| 6,743,187 B2 | 6/2004 | Solomon et al. |
| 6,946,812 B1 | 9/2005 | Martin et al. |
| 7,106,313 B2 | 9/2006 | Schena et al. |
| 7,224,642 B1 | 5/2007 | Tran et al. |
| 7,725,175 B2 | 5/2010 | Koeneman et al. |
| 7,883,479 B1 | 2/2011 | Stanley et al. |
| 8,286,723 B2 | 10/2012 | Puzio et al. |
| 8,308,664 B2 | 11/2012 | Pathak et al. |
| 9,074,847 B1 | 7/2015 | Sullivan et al. |
| 2001/0012932 A1 | 8/2001 | Peer |
| 2003/0006357 A1 | 1/2003 | Kaiser et al. |
| 2003/0036805 A1 | 2/2003 | Senior |
| 2003/0209678 A1 | 11/2003 | Pease |
| 2005/0113652 A1 | 5/2005 | Stark et al. |
| 2005/0171553 A1 | 8/2005 | Schwarz et al. |
| 2006/0044942 A1 | 3/2006 | Brinn et al. |
| 2006/0241510 A1 | 10/2006 | Halperin et al. |
| 2006/0259269 A1* | 11/2006 | Binder ............... B23Q 17/2428 702/155 |
| 2007/0050139 A1 | 3/2007 | Sidman |
| 2007/0109783 A1 | 5/2007 | Wilson et al. |
| 2007/0270784 A1 | 11/2007 | Smith et al. |
| 2009/0031839 A1 | 2/2009 | Shimizu et al. |
| 2009/0173351 A1 | 7/2009 | Sahin et al. |
| 2009/0203972 A1 | 8/2009 | Heneghan et al. |
| 2009/0227925 A1 | 9/2009 | McBean et al. |
| 2009/0254003 A1 | 10/2009 | Buckman |
| 2009/0276058 A1 | 11/2009 | Ueda et al. |
| 2010/0013860 A1 | 1/2010 | Mandella et al. |
| 2010/0036384 A1 | 2/2010 | Gorek et al. |
| 2010/0079101 A1 | 4/2010 | Sidman |
| 2010/0130873 A1 | 5/2010 | Yuen et al. |
| 2010/0198362 A1 | 8/2010 | Puchhammer |
| 2010/0228362 A1 | 9/2010 | Pathak et al. |
| 2010/0274365 A1 | 10/2010 | Evans et al. |
| 2011/0112442 A1 | 5/2011 | Meger et al. |
| 2012/0139456 A1 | 6/2012 | Takano et al. |
| 2012/0249310 A1 | 10/2012 | Hotaling |
| 2012/0259578 A1* | 10/2012 | Bevilacqua ........... G06F 1/1694 702/141 |
| 2013/0060124 A1 | 3/2013 | Zietsma |
| 2013/0060278 A1 | 3/2013 | Bozung et al. |
| 2013/0118320 A1 | 5/2013 | Richardson |
| 2013/0123666 A1 | 5/2013 | Giuffrida et al. |
| 2013/0123684 A1 | 5/2013 | Giuffrida et al. |
| 2013/0123759 A1 | 5/2013 | Kang et al. |
| 2013/0297022 A1* | 11/2013 | Pathak ...................... A61F 2/08 623/14.13 |
| 2014/0052275 A1 | 2/2014 | Pathak |
| 2014/0171834 A1 | 6/2014 | DeGoede et al. |
| 2014/0257047 A1 | 9/2014 | Sillay et al. |
| 2014/0257141 A1 | 9/2014 | Giuffrida et al. |
| 2014/0267778 A1* | 9/2014 | Webb ................... H04N 5/2328 348/169 |
| 2014/0303605 A1 | 10/2014 | Boyden et al. |
| 2014/0303660 A1* | 10/2014 | Boyden ................. A61B 17/32 606/170 |
| 2016/0242679 A1 | 8/2016 | Pathak et al. |

FOREIGN PATENT DOCUMENTS

| | | |
|---|---|---|
| CN | 103906483 A | 7/2014 |
| JP | 2008-67936 | 3/2008 |
| JP | 2008-238338 | 10/2008 |
| JP | 2010-118798 A | 5/2010 |
| KR | 101659554 B1 | 9/2016 |
| WO | WO 00/052355 | 9/2000 |
| WO | WO 00/78263 A2 | 12/2000 |
| WO | WO 2013/049020 A1 | 4/2013 |
| WO | WO 2014/113813 A1 | 7/2014 |
| WO | WO 2015/003133 A1 | 1/2015 |
| WO | 2016/133621 A1 | 8/2016 |

OTHER PUBLICATIONS

Kostikis, N. et al.—"Smartphone-based evaluation of parkinsonian hand tremor: Quantitative measurements vs clinical assessment scores", 2014 36th Annual International Conference of the IEEE Engineering in Medicine and Biology Society, IEEE, Aug. 26, 2014, pp. 906-909.
Louis, E.D., "Essential Tremor", Handbook of Clinical Neurology, vol. 100, 2011, pp. 433-448.
Louis, E.D., et al., "How common is the most common adult movement disorder estimates of the prevalence of essential tremor throughout the world", Movement Disorders, 1998, 13(1): p. 5-10.
Louis, E.D., et al., "Correlates of Functional Disability in Essential Tremor", Movement Disorders, 2001, 16(5): p. 914-920.
Mario Manto, et al., "Dynamically Responsive Intervention for Tremor Suppression", IEEE Engineering in Medicine and Biology Magazine, 2003, 22(3): p. 120-132.
Rubia P Meshack, et al., "A randomized controlled trial of the effects of weights on amplitude and frequency of postural hand tremor in people with Parkinson's disease", Clinical Rehabilitation, 2002, 16(5): p. 481-492.
National Parkinson Foundation, Treatment options, 2009, http://www.parkinson.org/Parkinson-s-Disease/Treatment.
Pathak, A. et al., "Measurement and Collection of Human Tremors Through a Handheld Tool" U.S. Appl. No. 14/627,893, filed Feb. 20, 2015, whole document.
Pathak, A. et al., "Handheld Tool for Leveling Uncoordinated Motion" U.S. Appl. No. 14/668,516, filed Mar. 25, 2015, whole document.
Pathak, A. et al., "A Noninvasive Handheld Assistive Device to Accommodate Essential Tremor: A Pilot Study," Brief Report, Movement Disorders, May 2014; 29(6):838-42. doi: 10.1002/mds. 25796.

(56) References Cited

OTHER PUBLICATIONS

Pathak et al. "Dynamic characterization and single-frequency cancellation performance of SMASH (SMA actuated stabilizing handgrip)." In: Modeling, Signal Processing, and Control for Smart Structures, Proceedings of SPIE, vol. 6926, 2008, pp. 692602-1 through 692602-12 [online]. Retrieved on Nov. 26, 2012 (Nov. 26, 2012). Retrieved from the Internet at URL:<http://144.206.159.178/ft/CONF/16413457/16413459.pdf>, entire document.
Pedley, Mark, "Tilt Sensing Using a Three-Axis Accelerometer", Freescale Semiconductor, Inc. Application Note, Document No. AN3461, Rev. 6, Mar. 2013, 22 pages.
Cameron N. Riviere, et al., "Toward Active Tremor Canceling in Handheld Microsurgical Instruments", IEEE Transactions on Robotics and Automation, vol. 19, No. 5, Oct. 2003, p. 793-800.
Eduardo Rocon, et al., "Mechanical suppression of essential tremor", The Cerebellum, 2007, 6(1): p. 73-78.
E. Rocon, et al., "Rehabilitation Robotics: a Wearable Exo-Skeleton for Tremor Assessment and Suppression", Proceedings of the 2005 IEEE International Conference on Robotics and Automation, 2005, p. 2271-2276.
E. Rocon, et al., "Theoretical Control Discussion on Tremor Suppression via Biomechanical Loading", 2003.
Shaw et al. "A reduced-order thermomechanical model and analytical solution for uniaxial shape memory alloy wire actuators." In: Smart Materials and Structures, vol. 18, 2009, pp. 1-21 [online]. Retrieved on Nov. 26, 2012 (Nov. 26, 2012). Retrieved from the Internet at URL:<hltp://deepblue.lib.umich.edu/bitstream/2027.42/65088/2/ sms9_6_065001.pdf>, entire document, especially Fig. 1b; p. 3, col. 1.
Sharon Smaga, "Tremor", American Family Physician, vol. 68, No. 8, Oct. 15, 2003, p. 1545-1552.
Umemura, A. et al., "Deep Brain Stimulation for Movement Disorders: Morbidity and Mortality in 109 Patients", J Neurosurg 98: 779-784, 2003.
Wireless & Mobile Human Monitoring, Latency Tech Note—Wireless Physiological Monitoring, Motion Sensor Latencies for Software Development, 4 pages retrieved from internet Feb. 3, 2015, http://glneurotech.com/bioradio/latency-tech-note/.
Wireless & Mobile Human Monitoring, Wireless motion sensor for 3D data acquisition via Bluetooth technology, Wireless Motion Sensor, 3 pages retrieved from internet Feb. 3, 2015, http://glneurotech.com/bioradio/physiological-signal-monitoring/wireless-motion-sensor/.
CA 2,951,338—First Examiner's Report dated Jan. 29, 2018, 4 pages.
U.S. Appl. No. 13/250,000—Restriction Requirement, dated Dec. 19, 2012, 9 pages.
U.S. Appl. No. 13/250,000—Non-Final Office Action, dated Apr. 5, 2013, 15 pages.
U.S. Appl. No. 13/250,000—Final Office Action, dated Mar. 20, 2014, 17 pages.
U.S. Appl. No. 13/250,000—Non-Final Office Action, dated Apr. 2, 2015, 19 pages.
U.S. Appl. No. 13/250,000—Notice of Allowance, dated Oct. 1, 2015, 5 pages.
U.S. Appl. No. 13/250,000—Non-Final Office Action, dated Oct. 19, 2016, 9 pages.
U.S. Appl. No. 13/250,000—Non-Final Office Action, dated Apr. 6, 2016, 13 pp.
U.S. Appl. No. 13/935,387—Non-Final Office Action, dated Apr. 3, 2015, 25 pages.
U.S. Appl. No. 13/935,387—Notice of Allowance, dated Oct. 7, 2015, 5 pages.
U.S. Appl. No. 13/935,387—Non-Final Office Action, dated Apr. 12, 2016, 13 pages.
U.S. Appl. No. 13/935,387—Final Office Action, dated Oct. 21, 2016, 10 pages.
PCT/US2012/057048—International Search Report and Written Opinion of the International Searching Authority, dated Dec. 17, 2012.
PCT/US2012/057048, PCT International Preliminary Report on Patentability, dated Apr. 1, 2014, 5 pages.
PCT/US2014/045409—International Search Report and Written Opinion of the International Searching Authority, dated Nov. 3, 2014, 9 pages.
PCT/US2014/045409, PCT International Preliminary Report on Patentability, dated Jan. 14, 2016, 8 pages.
JP 2014-533640—Notice of Allowance, dated Dec. 2, 2014, 3 pages.
JP 2014-533640—First Japanese Office Action, dated Mar. 31, 2015, 2 pages.
AU 2012316278—Australian Examination Report, dated Jul. 24, 2014, 3 pages.
AU 2012316278—Australian Notice of Acceptance, dated Jan. 15, 2015, 2 pages.
AU 2012316278—Australian Notice of Grant, dated May 14, 2015, 2 pages.
CN 2012-80047035.X—First Chinese Office Action, with English Translation, dated Apr. 28, 2015, 10 pages.
CN 2012-80047035.X—Second Chinese Office Action, with English Translation, dated Sep. 14, 2015, 11 pages.
CN 201280047035X—Third Office Action with English translation, dated Feb. 26, 2016, 8 pages.
EP 12834632.7—European Search Report, dated Jun. 10, 2015, 5 pages.
PCT/US2015/025781—International Search Report and Written Opinion of the International Searching Authority, dated Jul. 1, 2015.
PCT/US2015/025781—International Preliminary Report on Patentability, dated Nov. 3, 2016, 9 pages.
KR 10-2014-7011131—First Office Action, with English translation, dated Aug. 20, 2015, 7 pages.
PCT/US2016/013704—International Search Report and Written Opinion, dated Apr. 6, 2016, 19 pages.
EP 12834632.7—Examination Report, dated Oct. 18, 2016, 5 pages.
JP 2016-000701—First Office Action, with English Translation, 15 pages, dated Jan. 10, 2017.
Ahmad Anouti, et al., "Tremor Disorders Diagnosis and Management", Western Journal of Medicine, 1995, 162(6): p. 510-513.
Olivier W. Bertacchini, et al., "Fatigue life characterization of shape memory alloys undergoing thermomechanical cyclic loading", Smart Structures and Materials 2003, 2003. 5053: p. 612-624.
Mitchell F. Brin, et al., "Epidemiology and Genetics of Essential Tremor", Movement Disorders, 1998. 13(S3): p. 55-63.
DC-Micromotors, Application Datasheet, 0615 4.5S. 2010; available from: http://www.micromo.com.
Deuschl, G. et al., "Treatment of Patients with Essential Tremor", Lancet Neural of 2011, 10: 148-161.
Diamond, A., et al., "The effect of deep brain stimulation on quality of life in movement disorders", Journal of Neurology, Neurosurgery & Psychiatry, 2005, 76(9): p. 1188-1193.
Rodger J. Elble, "Physiologic and essential tremor", Neurology, 1986, 36(2): p. 225-231.
Rodger J. Elble, et al., "Essential tremor frequency decreases with lime", Neurology, 2000, 55(10): p. 1547-1551.
Caroline GL Gao, et al., "Robotics in Healthcare: HF Issues in Surgery," 2007, Online paper, http://ase.tufls.edu/mechanicai/EREL/Publications/D-4.pdf, 33 pages.
Great Lakes Neurotechnologies, Press Release "Great Lakes Neurotechnologies Awarded Patent for Sensor Based Continuous Parkinsons Assessment During Daily Activities", Dec. 3, 2013, 2 pages. www.glneurotech.com.
Mark Heath, et al., "Design Considerations in Active Orthoses for Tremor Suppression: Ergonomic Aspects and Integration of Enabling Technologies", Assistive Technology—Shaping the Future AAATE, 2003, p. 842-846.
Notice of Reasons for Rejection for corresponding Japanese Patent Application No. 2016-245290 dated Jun. 8, 2018, 12 pages.
AU 2016273988—First Examination Report dated Jul. 5, 2017, 3 pages.
U.S. Appl. No. 13/935,387—Non-Final Office Action, dated Apr. 6, 2017, 14 pages.
U.S. Appl. No. 14/668,516—Non-Final Office Action, dated May 30, 2017, 20 pages.

(56) References Cited

OTHER PUBLICATIONS

Chinese Office Action, with English Translation, for corresponding Chinese Patent Application No. 201611272927.6, dated Oct. 8, 2019, 34 pages.

* cited by examiner

HANDHELD TOOL FOR LEVELING UNCOORDINATED MOTION

CROSS REFERENCE TO RELATED APPLICATION

The present patent application is a divisional of U.S. application Ser. No. 14/668,516, filed on Mar. 25, 2015, the contents of which are hereby incorporated by reference.

TECHNICAL FIELD

This disclosure relates generally to tools for leveling or stabilizing muscle movements.

BACKGROUND INFORMATION

Motor impairment is a partial or total loss of function of a body part, usually a limb. This is often caused by muscle weakness, poor stamina, or a lack of motor control. It is often a symptom of neurological disorders such as Parkinson's Disease, ALS, stroke, Multiple Sclerosis, or Cerebral Palsy. There are few, if any effective, technologies available to assist with motor impairment and limitations in movement. As a result, many individuals are unable to conduct simple tasks such as feeding themselves, forcing them to rely on a caregiver.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system, and method of operation for providing auto-leveling of a user-assistive device of a handheld tool are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Technologies to help with human tremors have been developed, but they may be unsuitable for a variety of conditions where the human tremor is too extreme in magnitude, or the motor impairment results in tipping/spilling due to lack of muscle control. Stabilized platforms using inertial measurement units ("IMU") have been developed for cameras (e.g., brushless gimbal controllers) both in military applications and for hobbyists. Stabilized flight controllers similarly stabilize a moving platform in three-dimensional space. However, these solutions are not viable for integration into a small lightweight handheld tool to help people with muscle strength or muscle control limitations perform everyday tasks such as eating, drinking, or otherwise. Furthermore, certain occupations (e.g., surgical field) can benefit from tool leveling and/or stabilization particularly in high stress environments like an operating room or even a mobile army surgical hospital.

Figure 1A:
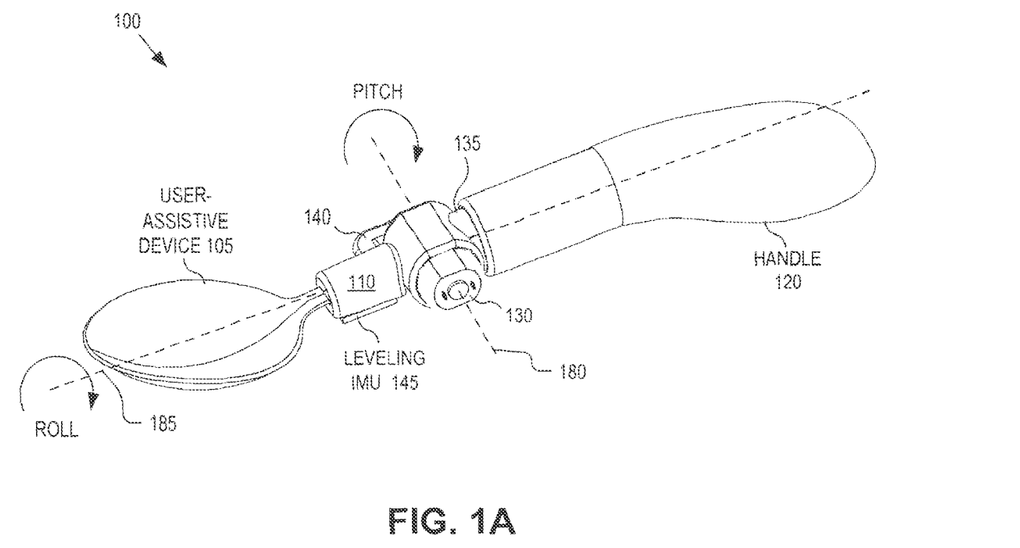
FIG. 1A is a perspective view illustration of a handheld tool that provides auto-leveling to a user-assistive device, in accordance with an embodiment of the disclosure.
Figure 1B:
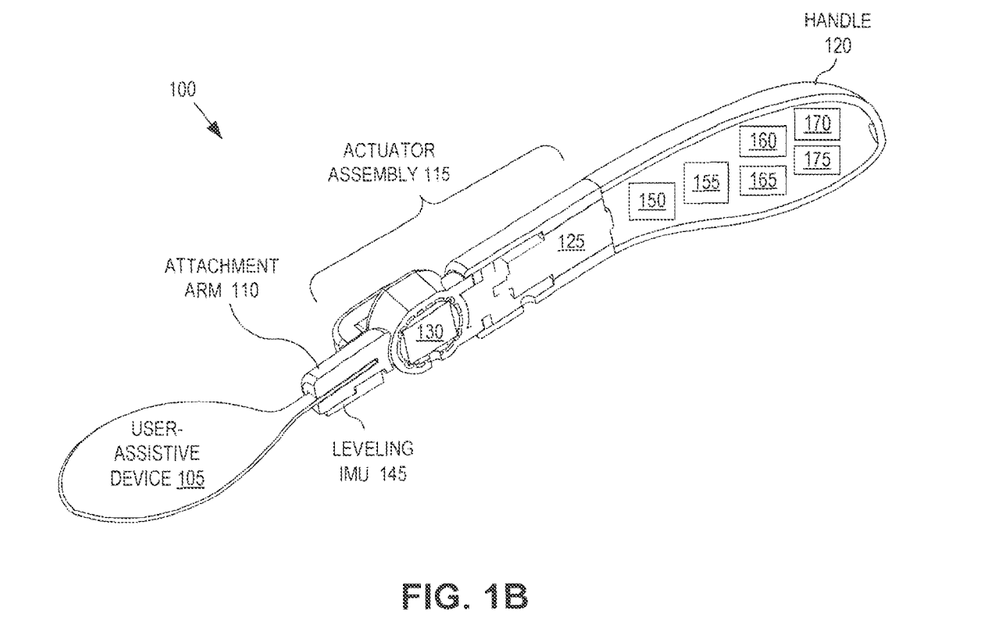
FIG. 1B is a cutaway perspective view illustration of a handheld tool that provides auto-leveling to a user-assistive device, in accordance with an embodiment of the disclosure.
Figure 1C:
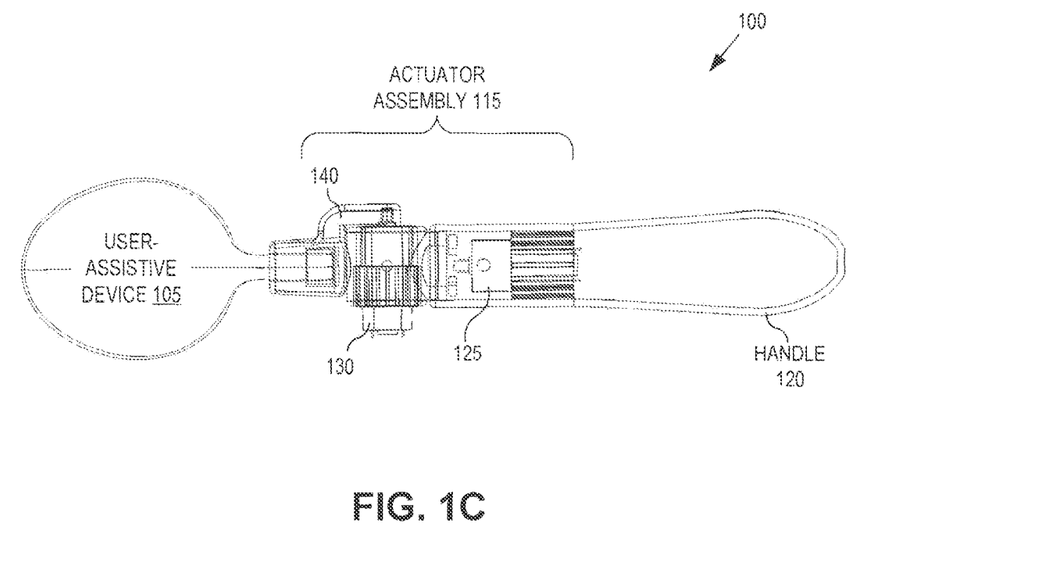
FIG. 1C is a plan view illustration of a handheld tool that provides auto-leveling to a user-assistive device, in accordance with an embodiment of the disclosure.
Figure 1D:
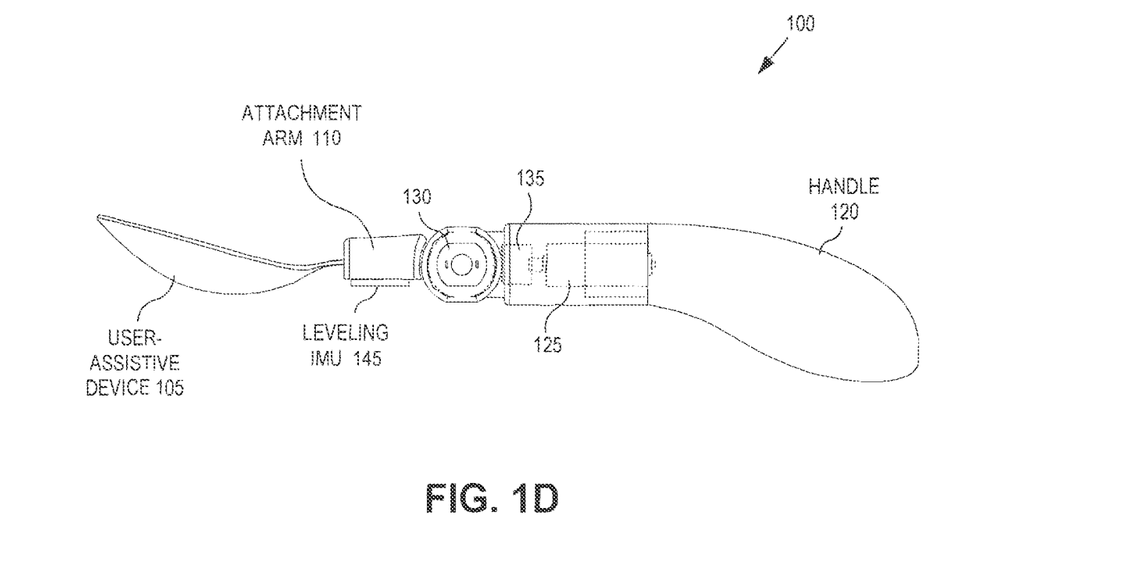
FIG. 1D is a side view illustration of a handheld tool that provides auto-leveling to a user-assistive device, in accordance with an embodiment of the disclosure.

FIGS. 1A-D illustrate a handheld tool 100 that is capable of auto-leveling, and in some embodiments stabilizing, a user-assistive device 105 connected to an end of handheld tool 100, in accordance with an embodiment of the disclosure. FIG. 1A is a perspective view illustration of handheld tool 100 while FIG. 1B is a cutaway perspective view illustration, FIG. 1C is a plan view illustration, and FIG. 1D is a side view illustration all of the same embodiment of handheld tool 100. The illustrated embodiment of handheld tool 100 includes a user-assistive device 105, an attachment arm 110, an actuator assembly 115, a handle 120, and a system circuitry. The illustrated embodiment of actuator assembly 115 includes actuator 125, actuator 130, linkage 135, and linkage 140. System circuitry includes a leveling IMU 145, a motion control system 150, a power supply 155, position sensors (not illustrated in FIGS. 1A-1D), a system controller 160, system memory 165, and a communication interface 170. In one embodiment, handheld tool 100 may also include a tremor IMU 175.

Figure 4:
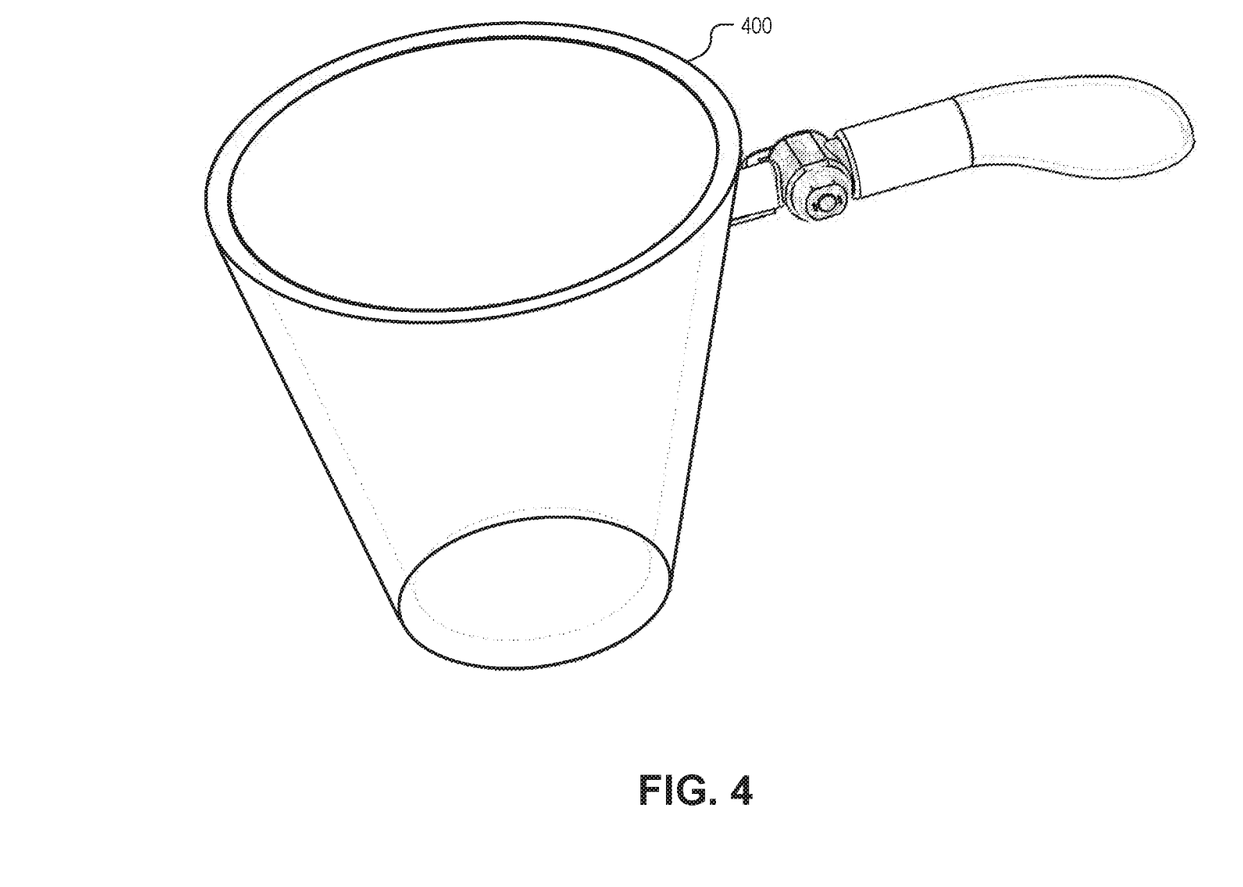
FIG. 4 is a perspective view illustration of a handheld tool with a user-assistive device fashioned to hold a cup for drinking, in accordance with an embodiment of the disclosure.

Handheld tool 100 is an auto-leveling (and in some embodiments tremor stabilizing) platform that can be adapted to hold a variety of different user-assistive devices 105. Handheld tool 100 provides active leveling using electronic actuators and a feedback control system. FIGS. 1A-D illustrates user-assistive device 105 as a spoon; however, user-assistive device 105 may be implemented as a variety of different eating utensils, drinking utensils (e.g., see cup-holder device 400 in FIG. 4), a makeup applicator, a pointing device, various occupational tools (e.g., surgical tools), or otherwise.

The illustrated embodiment of handheld tool 100 includes leveling IMU 145 disposed on attachment arm 145, which is rigidly connected to user-assistive device 105 to measure motions and orientation of user-assistive device 105. Leveling IMU 145 outputs feedback data indicative of the measured motions and orientation to motion control system 150. Leveling IMU 145 may be implemented with a gyroscope and accelerometer, or even additionally include a magnetometer. In one embodiment, leveling IMU 145 is a solid-state device.

In one embodiment, motion control system 150 polls leveling IMU 145 for linear accelerations, angular velocity, and orientation relative to a frame of reference (e.g., gravity vector) of user-assistive device 105 at a given instant. Motion control system 150 then executes an algorithm to estimate the orientation of user-assistive device 105 in three-dimensional ("3D") space relative to the frame of reference. This estimation or estimated vector of gravity relative to the body-frame of the leveling IMU (and user-assistive device 105) is continually updated in real-time and used to generate command signals for driving and controlling actuator assembly 115 in real-time. In one embodiment, the command signals include a roll command and a pitch command.

Actuator assembly 115 is connected to user-assistive device 105 to manipulate user-assistive device 105 in at least two orthogonal dimensions. In the illustrated embodiment, the two orthogonal dimensions include rotation about a pitch axis 180 and rotation about a roll axis 185. The pitch axis 180 is orthogonal to roll axis 185, which runs longitudinally through handle 120. In other embodiments, the two motion dimensions need not be orthogonal. Furthermore, in yet other embodiments, additional degrees of freedom may be added to actuator assembly 115 such as linear motions or even a yaw rotation.

Actuator assembly 115 is present in handheld tool 100 to move attachment arm 110 and by extension user-assistive device 105 relative to handle 120 for auto-leveling, and in some embodiments, tremor stabilization. If user-assistive device 105 is pitched or rolled relative to the fixed reference frame (e.g., gravity vector), the motion control system 150 will command actuator assembly 115 to move user-assistive device 105 in opposite directions to compensate and retain a level orientation or even provide an offsetting orientation to counteract a tremor. The overall effect is user-assistive device 105 remains fixed in orientation (or even stabilized), regardless of how the handle is oriented within physical limits of actuator assembly 115.

The illustrated embodiment of actuator assembly 115 includes actuator 125 which provides output rotational motion about roll axis 185. This roll motion is coupled to actuator 130 via a linkage 135 such that actuator 125 physically rotates actuator 130 about roll axis 185. The illustrated embodiment of actuator 130 provides output rotational motion about pitch axis 180. The pitch and roll motions are coupled to attachment arm, and by extension user-assistive device 105, via linkage 140 such that actuator 130 pitches user-assistive device 105 while actuator 125 rolls user-assistive device 105. These orthogonal rotational motions are independently controlled.

In one embodiment, handheld tool 100 further includes two position sensors that provide feedback positional information to motion control system 150 that is indicative of the rotational positions of the outputs of actuators 125 and 130 relative to handle 120. In other words, the positional sensors indicate the positions of linkages 135 and 140 relative to handle 120. In one embodiment, each positional sensor is a hall-effect sensor that monitors the positions of its respective linkage 135 or 140. Other positional sensors may be implemented including potentiometers, encoders, etc.

Conventional stabilizing devices attempt to provide stabilization using a weighted pendulum. However, a heavy mass is required to force the platform to rest in a level state. Disadvantages to such implementations include a required bulk and mass and the potential of swinging or oscillating of the pendulum at its natural frequency. The set-point (stabilized position) of the user assistive device is also limited by the mechanical assembly and cannot be easily adjusted. Furthermore, data about the user cannot be collected through these purely mechanical means. In contrast, the feedback control system used in handheld tool 100 can achieve much greater performance in a significantly smaller form-factor. Heavy weights are not required, and motion control system 150 can be specially tuned to react to various unintended motion (e.g., tremor stabilization). In fact, motion control system 150 can be programmed to respond to both uncoordinated movements (low frequency) for auto-leveling and unintentional movements (high frequency) for stabilization of human tremors.

Additionally, system controller 160 can be programmed to monitor and collect data about the severity of the user's condition (e.g., ability to maintain a level orientation, amount of feedback control assistance needed, amount of unintentional tremor motions, etc.) and store this data into a log within system memory 165 for eventual output via communication interface 170. The log can be analyzed and provided to a healthcare provider to diagnose and treat the user/patient's condition. The active control provided by motion control system 150 can further be programmed to automatically adjust in small increments overtime as part of a therapy plan. The therapy plan can be monitored using the log and tailored on a per patient basis by referring to the log. For example, the amount of active leveling/stabilization may be incrementally reduced at a prescribed rate as a sort of therapy or training and the results periodically monitored with reference to the log.

In one embodiment, attachment arm 110 is implemented as a permanent, fixed connection to a single user-assistive device 105. In other embodiments, attachment arm 110 may facilitate a non-permanent attachment to remove or replace user-assistive devices 105. Using a non-permanent attachment enables the user to insert or attach different types of user-assistive devices 105 to handheld tool 100. For example, user-assistive device 105 may be implemented as a variety of different eating or drinking utensils (e.g., spoon, knife, fork, cup-holder), personal hygiene tools (e.g., toothbrush, floss pick), grooming tools (e.g., makeup applicator, comb), occupational tools (e.g., surgical tools), pointing devices (e.g., laser pointer or stick pointer), or otherwise. The auto-leveling (and optional tremor stabilization) functionality can help users who have uncoordinated (and/or unintentional) muscle movements to have improved quality of life by providing greater independence and self-control over routine tasks. Furthermore, handheld tool 100 may have occupational uses that aid those that do not suffer from uncoordinated/unintentional muscle movements.

Figure 2:
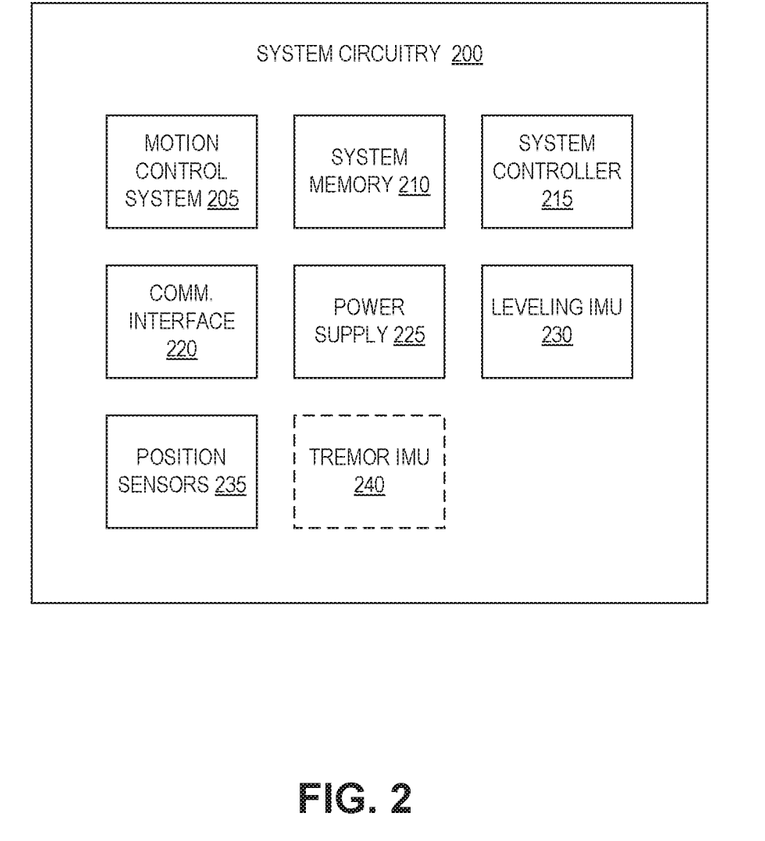
FIG. 2 is a functional block diagram illustrating components of system circuitry of a handheld tool that provides auto-leveling to a user-assistive device, in accordance with an embodiment of the disclosure.

FIG. 2 is a functional block diagram illustrating functional components of system circuitry 200, in accordance with an embodiment of the disclosure. System circuitry 200 illustrates example functional control components for the operation of handheld tool 100. The illustrated embodiment of system circuitry 200 includes a motion control system 205, system memory 210, a system controller 215, a communication interface 220, a power supply 225, a leveling IMU 230, position sensors 235, and a tremor IMU 240.

As discussed above, motion control system 205 receives (e.g., polls) feedback data from leveling IMU 230 to determine the orientation and motion of user-assistive device 105. This feedback data is analyzed using a control algorithm to generate commands for manipulating actuator assembly 115. In one embodiment, motion control system 205 is implemented as digital signal processing ("DSP") circuit. In another embodiment, motion control system 205 is software/firmware logic executed on system controller 215 and stored in system memory 210. In one embodiment, system controller 215 is implemented as a microprocessor and system memory 210 is non-volatile memory (e.g., flash memory). Other types of memory and controllers may be used.

In one embodiment, communication interface 220 is communicatively coupled to system controller 215 to output data (e.g., usage log) stored in system memory 210. Communication interface 220 may be implemented as a wired or wireless interface, such as a universal serial port ("USB"), a wireless Bluetooth interface, a WiFi interface, a cellular interface, or otherwise.

As mentioned above, leveling IMU 230 is disposed to monitor the orientation and motion of user-assistive device 105. In the illustrated embodiment of FIGS. 1A-D, leveling IMU 145 is disposed on attachment arm 145. In an embodiment where user-assistive device 105 is permanently fixed to handheld tool 100, leveling IMU 230 may also be rigidly mounted to user-assistive device 105 itself or attachment arm 110 may be considered an extension piece of user-assistive device 105. Leveling IMU 230 may be implemented as a solid-state sensor including one or more of an accelerometer, a gyroscope, or a magnetometer.

Position sensors 235 are relative sensors that measure the relative positions of the outputs of actuator assembly 115 relative to handle 120. In one embodiment, position sensors 235 are hall-effect sensors that monitor the position of the outputs of actuators 125 and 130 by measuring the positions of linkages 135 and 140. The relative position information output by position sensors 235 may be recorded to a log within system memory 210 for determining how much auto-leveling a user needs and thereby diagnosing the severity and progress of a given user.

In one embodiment, handheld tool 100 may further include tremor IMU 240 rigidly mounted to handle 120 to measure the motion/orientation of handle 100. The tremor feedback information acquired by tremor IMU 240 may also be recorded to a log file within system memory 210 to facilitate diagnosis and treatment of a user's condition. In some embodiments, feedback data from tremor IMU 240 may also be used for feedback stabilization, though feedback data from leveling IMU 230 may be sufficient and even preferable for both auto-leveling and stabilization of user-assistive device 100.

In the illustrated embodiment, the functional components of system circuitry 200 are powered by power supply 225. In one embodiment, power supply 225 is a rechargeable battery (e.g., lithium ion battery) disposed within handle 120 of handheld tool 100. Many of the other functional components of system circuitry 200 may also be disposed within handle 120 to provide a compact, user friendly form factor. For example, in various embodiments, some or all of motion control system 205, system memory 210, system controller 215, communication interface 220, power supply 225, and tremor IMU 240 are disposed within handle 120. As illustrated in FIGS. 1A-D, actuator 125 and linkage 135 are at least partially disposed within handle 120.

Figure 3:
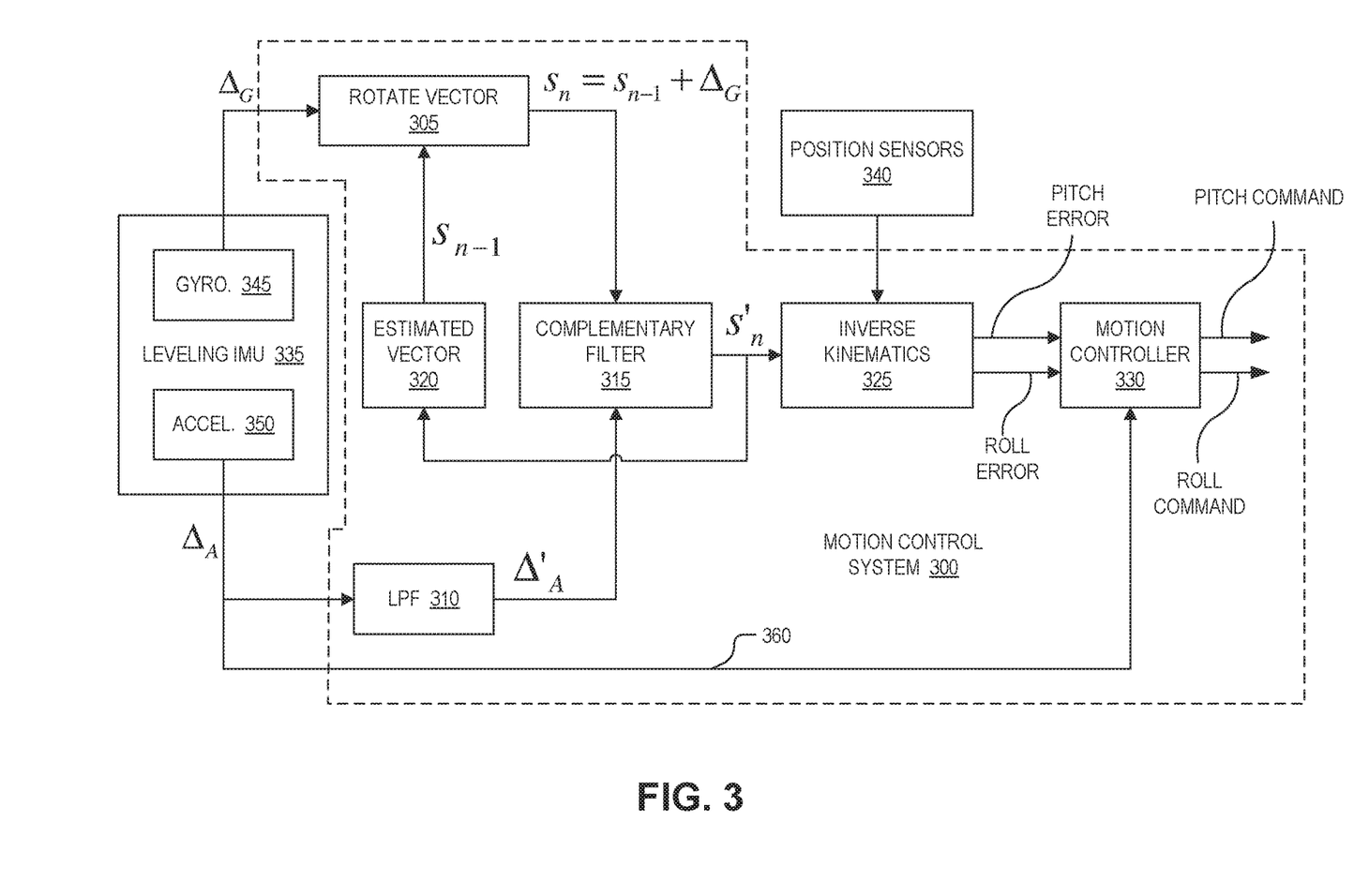
FIG. 3 is a functional block diagram illustrating components of a motion control system for providing auto-leveling to a user-assistive device of a handheld tool, in accordance with an embodiment of the disclosure.

FIG. 3 is a functional block diagram illustrating functional components of a motion control system 300 for providing auto-leveling to user-assistive device 105 of a handheld tool 100, in accordance with an embodiment of the disclosure. Motion control system 300 is one possible implementation of motion control systems 150 or 205. Motion control system 300 may be implemented as software logic/instructions, as firmware logic/instructions, as hardware logic, or a combination thereof. In one embodiment, motion control system 300 is a DSP circuit.

The illustrated embodiment of motion control system 300 includes a rotate vector module 305, a low pass filter ("LPF") 310, a complementary filter module 315, an estimated vector module 320, an inverse kinematics module 325, and a motion controller 330. Motion control system 300 is coupled to receive feedback data from leveling IMU 335 and position sensors 340. The illustrated embodiment of leveling IMU 335 includes a gyroscope 345 and an accelerometer 350.

During operation, gyroscope 345 outputs gyro data $\Delta_G$ while accelerometer 350 outputs accelerometer data $\Delta_A$. The gyro data $\Delta_G$ is used by rotate vector module 305 to adjust a previous error vector $S_{n-1}$ to generate a current error vector $S_n$. The current error vector $S_n$ is then provided to complementary filter module 315. Complementary filter module 315 adjusts the current error vector $S_n$ with a low pass filtered version $\Delta'_A$ of the accelerometer data $\Delta_A$ to generate an adjusted error vector $S'_n$. The adjust error vector $S'_n$ is looped back to estimated vector module 320 where it is latched or temporarily stored and provided to rotated vector module 305 as the previous error vector $S_{n-1}$ for the next cycle of operation.

The adjusted error vector $S'_n$ represents a difference vector between the frame of reference (e.g, gravity vector) and a vector representing the current position of user-assistive device 105. For example, the vector representing the current position of user-assistive device 105 may be a normal vector extending from a surface upon which leveling IMU 145 is disposed. Of course, other vector orientations for describing user-assistive device 105 may be used.

Gyroscope 345 is a rapid operation sensor that outputs angular velocity data quickly, but suffers from drift overtime. In contrast, accelerometer 350 is a slow sensor that outputs accurate readings that are used by complementary filter 315 to update the current error vector $S_n$ and cancel out any drift. Accelerometer data $\Delta_A$ is low pass filtered to remove high frequency changes due to sudden jerks, such as tremor motions, which are less useful for the low frequency auto-leveling function.

The adjusted error vector $S'_n$ is then provided to the inverse kinematics module 325. Inverse kinematics module 325 takes the adjusted error vector $S'_n$ along with the current position information of actuator assembly 115 and generates error signals (e.g., pitch error and roll error) that define the position parameters of actuators 125 and 130 to obtain the desired position of user-assistive device 105. The use of kinematic equations are known in the field of robotic control systems.

The error signals are then input into motion controller 330, which determines how to implement the actual commands (e.g., pitch command and roll command) for controlling actuator assembly 115. In one embodiment, motion controller 330 is implemented as a proportional-integral-derivative ("PID") controller. Motion controller 330 attempts to reducing the error signals (e.g., pitch error and roll error) while also reducing correction overshoot and oscillations.

In the illustrated embodiment, motion control system 300 also includes a high frequency path 360 for accelerometer data $\Delta_A$ to reach motion controller 330. High frequency path 360 permits unfiltered high frequency accelerometer data $\Delta_A$ to be analyzed by motion controller 330 to implement tremor stability control.

Some of the functional logic/software explained above is described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. At least one non-transitory machine-accessible storage medium that provides instructions that, when executed by a handheld tool, will cause the handheld tool to perform operations comprising:
    measuring at least one of a motion or an orientation of a user-assistive device mounted to a distal end of the handheld tool with an inertial measurement unit ("IMU");
    outputting feedback data from the IMU based upon the measuring, wherein the IMU includes a gyroscope and wherein the feedback data includes gyroscope feedback data;
    monitoring the feedback data in real-time with a motion control system at least partially disposed within a handle of the handheld tool; and
    controlling an actuator assembly with the motion control system, wherein the actuator assembly is coupled to manipulate the user-assistive device in at least two orthogonal dimensions to provide auto-leveling of the user-assistive device to a frame of reference while a user manipulates the handheld tool, wherein controlling the actuator assembly with the motion control system to provide auto-leveling includes:
        generating an error vector indicating a positional deviation of the user assistive device from a reference vector based upon the frame of reference;
        updating the error vector based upon the feedback data, including the gyroscope feedback data, output from the IMU; and generating one or more commands to manipulate the actuator assembly based at least in part upon the error vector.

2. The at least one machine-accessible storage medium of claim 1, wherein the at least two orthogonal dimensions comprise two rotational axes including a pitch axis and a roll axis.

3. The at least one machine-accessible storage medium of claim 2, wherein generating the one or more commands to manipulate the actuator assembly comprises:
    generating a pitch command to manipulate the actuator assembly about the pitch axis and a roll command to manipulate the actuator assembly about the roll axis based at least in part upon the error vector.

4. The at least one machine-accessible storage medium of claim 3, wherein the IMU includes an accelerometer, wherein the feedback data includes accelerometer feedback data, and wherein controlling the actuator assembly with the motion control system to provide auto-leveling further comprises:
    low pass filtering the accelerometer feedback data before updating the error vector with the accelerometer feedback data.

5. The at least one machine-accessible storage medium of claim 2, further providing instructions that, when executed by the handheld tool, will cause the handheld tool to perform further operations, comprising:
    controlling the actuator assembly with the motion control system about the two rotational axes to provide human tremor stabilization of the user-assistive device.

6. The at least one machine-accessible storage medium of claim 5, wherein controlling the actuator assembly with the motion control system about the two rotational axes to provide human tremor stabilization comprises:
    using accelerometer feedback data output from an accelerometer of the IMU without low pass filtering the accelerometer feedback data to provide feedback control for the human tremor stabilization.

7. The at least one machine-accessible storage medium of claim 2, further providing instructions that, when executed by the handheld tool, will cause the handheld tool to perform further operations, comprising:
    collecting position information from one or more position sensors coupled to monitor positions of the actuator assembly relative to the two rotations axes;
    recording the position information into a log; and
    communicating the log out of the handheld tool via a communication interface.

8. The at least one machine-accessible storage medium of claim 1, further providing instructions that, when executed by the handheld tool, will cause the handheld tool to perform further operations, comprising:
    adjusting an amount of active stabilization applied to the user-assistive device by the actuator assembly over time as part of a training plan or a therapy plan for treating the user.

9. The at least one machine-accessible storage medium of claim 8, wherein the amount of active stabilization applied by the actuator assembly is reduced over time as part of the therapy plan.

10. The at least one machine-accessible storage medium of claim 1, wherein a power supply is disposed within a handle of the handheld tool and coupled to power the actuator assembly and the motion control system and wherein the user-assistive device comprises either one of an eating utensil or a cup-holder.

11. A method implemented by a handheld tool, the method comprising:
  measuring at least one of a motion or an orientation of a user-assistive device mounted to a distal end of the handheld tool with an inertial measurement unit ("IMU");
  outputting feedback data from the IMU based upon the measuring, wherein the IMU includes an accelerometer and wherein the feedback data includes accelerometer feedback data;
  monitoring the feedback data in real-time with a motion control system at least partially disposed within a handle of the handheld tool; and
  controlling an actuator assembly with the motion control system, wherein the actuator assembly is coupled to manipulate the user-assistive device in at least two orthogonal dimensions to provide auto-leveling of the user-as sistive device to a frame of reference while a user manipulates the handheld tool, wherein controlling the actuator assembly with the motion control system to provide auto-leveling includes:
    generating an error vector indicating a positional deviation of the user-assistive device from a reference vector based upon the frame of reference;
    updating the error vector based upon the feedback data, including the accelerometer feedback data, output from the IMU;
    low pass filtering the accelerometer feedback data before updating the error vector with the accelerometer feedback data; and
    generating one or more commands to manipulate the actuator assembly based at least in part upon the error vector.

12. The method of claim 11, wherein the at least two orthogonal dimensions comprise two rotational axes including a pitch axis and a roll axis.

13. The method of claim 12, wherein generating the one or more commands to manipulate the actuator assembly comprises:
  generating a pitch command to manipulate the actuator assembly about the pitch axis and a roll command to manipulate the actuator assembly about the roll axis based at least in part upon the error vector.

14. The method of claim 13, wherein the IMU includes a gyroscope, wherein the feedback data includes gyroscope feedback data, and wherein controlling the actuator assembly with the motion control system to provide auto-leveling further comprises:
  updating the error vector with the gyroscope feedback data.

15. The method of claim 12, further comprising:
  controlling the actuator assembly with the motion control system about the two rotational axes to provide human tremor stabilization of the user-assistive device.

16. The method of claim 15, wherein controlling the actuator assembly with the motion control system about the two rotational axes to provide human tremor stabilization comprises:
  using accelerometer feedback data output from an accelerometer of the IMU without low pass filtering the accelerometer feedback data to provide feedback control for the human tremor stabilization.

17. The method of claim 12, further comprising:
  collecting position information from one or more position sensors coupled to monitor positions of the actuator assembly relative to the two rotations axes;
  recording the position information into a log; and
  communicating the log out of the handheld tool via a communication interface.

18. The method of claim 11, further comprising:
  adjusting an amount of active stabilization applied to the user-assistive device by the actuator assembly over time as part of a training plan or a therapy plan for treating the user.

19. The method of claim 18, wherein the amount of active stabilization applied by the actuator assembly is reduced over time as part of the therapy plan.

20. The method of claim 11, wherein a power supply is disposed within a handle of the handheld tool and coupled to power the actuator assembly and the motion control system and wherein the user-assistive device comprises either one of an eating utensil or a cup-holder.

21. At least one non-transitory machine-accessible storage medium that provides instructions that, when executed by a handheld tool, will cause the handheld tool to perform operations comprising:
  measuring at least one of a motion or an orientation of a user-assistive device mounted to a distal end of the handheld tool with an inertial measurement unit ("IMU"); outputting feedback data from the IMU based upon the measuring;
  monitoring the feedback data in real-time with a motion control system at least partially disposed within a handle of the handheld tool;
  controlling an actuator assembly with the motion control system, wherein the actuator assembly is coupled to manipulate the user-assistive device in at least two orthogonal dimensions to provide auto-leveling of the user-assistive device to a frame of reference while a user manipulates the handheld tool, wherein the at least two orthogonal dimensions comprise two rotational axes;
  collecting position information from one or more position sensors coupled to monitor positions of the actuator assembly relative to the two rotations axes;
  recording the position information into a log; and
communicating the log out of the handheld tool via a communication interface.

22. At least one non-transitory machine-accessible storage medium that provides instructions that, when executed by a handheld tool, will cause the handheld tool to perform operations comprising:
  measuring at least one of a motion or an orientation of a user-assistive device mounted to a distal end of the handheld tool with an inertial measurement unit ("IMU");
outputting feedback data from the IMU based upon the measuring;
  monitoring the feedback data in real-time with a motion control system at least partially disposed within a handle of the handheld tool;
  controlling an actuator assembly with the motion control system, wherein the actuator assembly is coupled to manipulate the user-assistive device in at least two orthogonal dimensions to provide auto-leveling of the user-assistive device to a frame of reference while a user manipulates the handheld tool; and adjusting an amount of active stabilization applied to the user-assistive device by the actuator assembly over time as part of a training plan or a therapy plan for treating the user.

\* \* \* \* \*